(12) United States Patent
Bishop

(10) Patent No.: US 6,215,011 B1
(45) Date of Patent: Apr. 10, 2001

(54) SILANE COMPOSITIONS

(75) Inventor: Craig V. Bishop, Lakewood, OH (US)

(73) Assignee: McGean-Rohco, Inc., Cleveland, OH (US)

( * ) Notice: Subject to any disclaimer, the term of this patent is extended or adjusted under 35 U.S.C. 154(b) by 0 days.

(21) Appl. No.: 08/376,282

(22) Filed: Jan. 20, 1995

Related U.S. Application Data

(63) Continuation of application No. 08/163,946, filed on Dec. 8, 1993, now abandoned.

(51) Int. Cl.$^7$ ............................................. C07F 7/02
(52) U.S. Cl. .................. 556/413; 556/418; 556/423; 556/427; 556/431; 556/435; 556/436
(58) Field of Search ................................ 556/413, 418, 556/423, 427, 431, 435, 436

(56) References Cited

U.S. PATENT DOCUMENTS

| | | | |
|---|---|---|---|
| 2,715,133 | 8/1955 | Speler | 260/448.2 |
| 2,832,754 | 4/1958 | Jex et al. | 260/46.5 |
| 2,920,095 | 1/1960 | Jex et al. | 260/448.8 |
| 3,469,982 | 9/1969 | Celeste | 96/35.1 |
| 4,410,669 | 10/1983 | Panster et al. | 525/474 |
| 4,499,152 | 2/1985 | Green et al. | 428/448 |
| 4,689,085 | 8/1987 | Plueddemann | 106/287.14 |
| 4,775,415 | 10/1988 | Mohr et al. | 106/14.05 |
| 5,051,129 | 9/1991 | Cuthbert et al. | 106/2 |
| 5,073,456 | 12/1991 | Palladino | 428/446 |
| 5,101,055 | 3/1992 | Dinh et al. | 556/413 |
| 5,187,134 | 2/1993 | Panster et al. | 502/158 |
| 5,205,860 | 4/1993 | Narula et al. | 106/2 |
| 5,286,527 | 2/1994 | Blum et al. | 427/407.1 |
| 5,302,458 | 4/1994 | Blum et al. | 428/429 |

FOREIGN PATENT DOCUMENTS

| | | |
|---|---|---|
| 0255227 | 2/1988 | (EP) . |
| 0431501 | 6/1991 | (EP) . |
| 0508610 | 11/1992 | (EP) . |
| 0515801 | 12/1992 | (EP) . |

OTHER PUBLICATIONS

Science, Jul. 2, 1993, vol. 261, No. 5117, pp. 6–7 and 73–76, "Directionally Aligned Helical Peptides on Surfaces," Whitesell et al.

Primary Examiner—Robert Dawson
(74) Attorney, Agent, or Firm—Renner, Otto, Boiselle & Sklar, LLP

(57) ABSTRACT

Silane compositions are described which comprise (A) a silane coupling agent; and (B) a tris(silylorgano)amine or alkane characterized by the formulae $$[(RO)_3SiR^1]_3N \qquad (I)$$

or $$[(RO)_3SiR^1]_3CR^2 \qquad (II)$$

wherein each R is independently an alkyl, alkoxyalkyl, aryl, aralkyl or cycloalkyl group of less than 20 carbon atoms; $R^1$ is a divalent hydrocarbon or polyether group of less than 20 carbon atoms; and $R^2$ is a functional group represented by $$C_nH_{2n}X$$

wherein n is from 0 to 20 and X is selected from the group consisting of amino, amido, hydroxy, alkoxy, halo, mercapto, carboxy, acyl, vinyl, allyl, styryl, epoxy, isocyanato, glycidoxy, and acryloxy groups. The silane compositions of the present invention are adhesive compositions providing improved bonding of surfaces such as glass, metal and metal oxides to thermosetting resins. The silane compositions also exhibit improved moisture resistance. The silane compositions are particularly useful as adhesives in preparing multi-layer laminates such as printed circuit boards.

26 Claims, No Drawings

SILANE COMPOSITIONS

This is a continuation of application(s) Ser. No. 08/163,946 filed on Dec. 8, 1993 and now abondoned.

TECHNICAL FIELD

This invention relates to silane compositions, and more particularly, to silane compositions comprising a silane coupling agent and a tris(silylorgano)amine or alkane. The silane compositions are useful as adhesives, and more particularly, as adhesives in the preparation of multi-layer laminates such as printed circuit boards (PCBs).

BACKGROUND OF THE INVENTION

Silane compositions and silane coupling agents are well known. The use of silane coupling agents can increase the adhesive characteristics of many bonds, particularly the bond of thermosetting resins to glass, metal and metal oxide surfaces. It is well known that the bond formed by silane coupling agents is often deleteriously affected by moisture and, occasionally, the exposure of silane-coupled bonds to humid conditions can lead to the premature failure of the bond.

To minimize the effect that moisture has on silane-coupled failures, cross-linking agents have been combined with the silane coupling agents. For example, U.S. Pat. No. 4,689,085 describes silane compositions which comprise (I) a silane coupling agent; and (II) a disilyl cross-linker compound represented by the general formula $$(RO)_3SiR'Si(OR)_3$$

wherein RO denotes an alkoxy group containing from 1 to 8 carbon atoms, R' is a divalent organic group, and the weight ratio of (I) to (I) is between 1:99 and 99:1 inclusive. The silane compositions are reported to be useful as primers in the production of laminates and other composite materials.

U.S. Pat. No. 5,073,456 describes multi-layer printed circuit boards and processes for preparing multi-layer printed circuit boards utilizing a silane bonding mixture consisting essentially of (I) a ureido silane, and (II) a disilyl cross-linking agent generally represented by the formula $$(RO)_3SiR'Si(OR)_3$$

wherein each R is an alkyl group containing 1 to 8 carbon atoms and R' is an alkylene group having from 1 to 8 carbon atoms.

Unfortunately, the disilyl cross-linking agents described in the '085 and '456 patents recently have been found to possess highly toxic properties as disclosed in several TSCA 8(e) submissions to the U.S. Environmental Protection Agency (for example, 8EHQ-0388-0347, 8EHQ-0392-1047, etc.). Therefore, the continued use of disilyl cross-linking agents must be closely examined and materials which can be substituted for the toxic disilyl cross-linking agents would be desirable.

SUMMARY OF THE INVENTION

Silane compositions are described which comprise (A) a silane coupling agent; and (B) a tris(silylorgano)amine or alkane characterized by the formulae $$[(RO)_3SiR^1]_3N \quad (I)$$

or $$[(RO)_3SiR^1]_3CR^2 \quad (II)$$

wherein each R is independently an alkyl, alkoxyalkyl, aryl, aralkyl or cycloalkyl group of less than 20 carbon atoms; $R^1$ is a divalent hydrocarbon or polyether group of less than 20 carbon atoms; and $R^2$ is a functional group represented by $$C_nH_{2n}X$$

wherein n is from 0 to 20 and X is selected from the group consisting of amino, amido, hydroxy, alkoxy, halo, mercapto, carboxy, acyl, vinyl, allyl, styryl, epoxy, isocyanato, glycidoxy, and acryloxy groups. The silane compositions of the present invention are adhesive compositions providing improved bonding of surfaces such as glass, metal and metal oxides to thermosetting resins. The silane compositions also exhibit improved moisture resistance. The silane compositions are particularly useful as adhesives in preparing multi-layer laminates such as printed circuit boards.

DESCRIPTION OF THE PREFERRED EMBODIMENTS

The silane compositions of the present invention contain at least one silane coupling agent. Silane coupling agents (A) are well known, and various conventional silane coupling agents can be utilized. In one embodiment, the silane coupling agents (A) are characterized by the formula $$A_{(4-x)}Si(B)_x \quad (III)$$

wherein A is a hydrolyzable group, x is 1, 2 or 3, and B is a monovalent organic group. The A groups are groups which hydrolyze in the presence of water and may include acetoxy groups, alkoxy groups containing up to 20 carbon atoms and chloro groups. In one preferred embodiment, x=1 and each A is an RO group such as represented by the formula $$(RO)_3SiB \quad (IIIA)$$

wherein each R is independently an alkyl, aryl, aralkyl or cycloalkyl group containing less than 20 carbon atoms, more often up to about 5 carbon atoms. The number of hydrolyzable groups A present in the silane coupling agent of Formula III may be 1, 2 or 3 and is preferably 3 (i.e., x=1). Specific examples of RO groups include methoxy, ethoxy, propoxy, methylmethoxy, ethylmethoxy, phenoxy, etc.

The Group B in Formula III may be an alkyl or aryl group, or a functional group represented by the formula $$C_nH_{2n}X$$

wherein n is from 0 to 20 and X is selected from the group consisting of amino, amido, hydroxy, alkoxy, halo, mercapto, carboxy, acyl, vinyl, allyl, styryl, epoxy, isocyanato, glycidoxy and acryloxy groups. The alkyl and aryl groups may contain up to about 10 carbon atoms. Alkyl groups containing from 1 to about 5 carbon atoms are particularly useful. In one embodiment, n is an integer from 0 to 10 and more often from 1 to about 5.

The amino groups may contain one or more nitrogen atoms and, thus, may be monoamino groups, diamino groups, triamino groups, etc. General examples of diamino silane coupling agents can be represented by the formula $$A_3SiR^4N(R^5)R^4N(R^5)_2 \quad (IIIC)$$

wherein A is as defined in Formula III, each $R^4$ is independently a divalent hydrocarbyl group containing from 1 to about 5 carbon atoms, and each $R^5$ is independently hydrogen or an alkyl or an aryl group containing up to about 10 carbon atoms. The divalent hydrocarbyl groups include methylene, ethylene, propylene, etc. Each $R^5$ is preferably hydrogen or a methyl or ethyl group.

The silane coupling agents which may contain amido groups include compositions represented by Formula III wherein the Group B may be represented by the formulae $$-R^4C(O)N(R^5)_2$$

and $$-R^4-N(R^5)C(O)N(R^5)_2$$

wherein each $R^4$ is independently a divalent hydrocarbyl group containing from 1 to 20 carbon atoms, more often from 1 to about 5 carbon atoms, and each $R^5$ is independently hydrogen or an alkyl or aryl group containing up to about 10 carbon atoms. Thus, the amido group may be an amide group or an ureido group. Generally, each $R^5$ in the formulae for the amido groups is hydrogen or an alkyl group containing from 1 to about 5 carbon atoms.

In one embodiment, the silane coupling agent is a ureido silane represented by the formula $$(RO)_3SiR^4N(H)CONH_2 \qquad \text{(IIIB)}$$

wherein each R is an alkyl group containing 1 to about 5 carbon atoms, particularly methyl or ethyl groups, and $R^4$ is a divalent hydrocarbyl group containing from 1 to about 5 carbon atoms. Examples of such divalent hydrocarbyl groups include methylene, ethylene, propylene, butylene, etc. Specific examples of such ureido silanes include β-ureidoethyl-trimethoxysilane; β-ureidoethyl-triethoxysilane; γ-ureidoethyl-trimethoxysilane; γ-ureidopropyl-triethoxysilane, etc.

Other examples of silane coupling agents useful in the present invention include N-(2-aminoethyl)-3-aminopropyltrimethoxysilane, 3-methacryloxypropyltrimethoxysilane, 3[2(vinylbenzylamino)ethylamino]-propyltrimethoxysilane, 3-glycidoxypropyltrimethoxysilane, triacetoxyvinylsilane, tris-(2-methoxyethoxy)vinylsilane, 3-chloropropyltrimethoxysilane, 1-trimethoxysilyl-2-(p,m-chloromethyl)phenyl-ethane, 3-chloropropyltriethoxysilane, N-(aminoethylaminomethyl)phenyltrimethoxysilane, N-(2-aminoethyl)-3-aminopropyl tris(2-ethylhexoxy)silane, 3-aminopropyltrimethoxysilane, trimethoxysilylpropylenetriamine, β(3,4-epoxycyclohexyl) ethyltrimethoxysilane, 3-mercaptopropyltrimethoxysilane, 3-mercaptotriethoxysilane, 3-mercaptopropylmethyldimethoxysilane, bis(2-hydroxyethyl)-3-aminopropyltrimethoxysilane, 1,3-divinyltetramethyldisilazane, vinyltrimethoxysilane, 2-(diphenylphosphino)ethyltriethoxysilane, 2-methacryloxyethyldimethyl[3-trimethoxysilylpropyl] ammonium chloride, 3-isocyanatopropyldimethylethoxysilane, N-(3-acryloxy-2-hydroxypropyl)-3-aminopropyltriethoxysilane, vinyl tris(t-butylperoxy)silane, methyltrimethoxysilane, ethyltrimethoxysilane, phenyltrimethoxysilane, phenyltriacetoxysilane, methyltrimethoxysilane, phenyltrimethoxysilane.

The preferred silane coupling agents (A) are those which are commercially available and which are recognized by those skilled in the art as being effective coupling agents. A number of organofunctional silanes are available, for example, from Union Carbide, Specialty Chemicals Division, Danbury, Conn. Examples of useful silane coupling agents available from Union Carbide are summarized in the following table.

TABLE I

Silane Coupling Agents

| Type | Trade Designation | Formula |
|---|---|---|
| Esters | A-137 | $(EtO)_3SiC_8H_{17}$ |
|  | A-162 | $(EtO)_3SiCH_3$ |
| Amino | A-1100 | $(EtO)_3Si(CH_2)_3NH_2$ |
|  | A-1110 | $(MeO)_3Si(CH_2)_3NH_2$ |
|  | A-1120 | $(MeO)_3Si(CH_2)_3NH(CH_2)_2NH_2$ |
|  | A-1130 | $(MeO)_3Si(CH_2)_3NH(CH_2)_2NH(CH_2)_2NH_2$ |
| Ureido | A-1160* | $(EtO)_3Si(CH_2)_3NHC(O)NH_2$ |
| Isocyanato | A-1310 | $(EtO)_3Si(CH_2)_3N=C=O$ |
| Vinyl | A-151 | $(EtO)_3SiCH=CH_2$ |
|  | A-171 | $(MeO)_3SiCH=CH_2$ |
|  | A-172 | $(CH_3OC_2H_4O)_3SiCH=CH_2$ |
| Methacryloxy | A-174 | $(MeO)_3Si(CH_2)_3OC(O)C(CH_3)=CH_2$ |
| Epoxy | A-187 |  |
| Mercapto | A-189 | $(MeO)_3Si(CH_2)_3SH$ |

*50% w/w in methanol

The second component in the silane compositions of the present invention is (B) a tris(silylorgano)amine characterized by the formula $$[(RO)_3SiR^1]_3N \qquad \text{(I)}$$

or a tris(silylorgano)alkane characterized by the formula $$[(RO)_3SiR^1]_3CR^2 \qquad \text{(II)}$$

wherein in Formulae I and II, each R is independently an alkyl, alkoxyalkyl, aryl, aralkyl or cycloalkyl group of less than 20 carbon atoms; $R^1$ is a divalent hydrocarbon or polyether group of less than 20 carbon atoms; and $R^2$ is a functional group represented by $$C_nH_{2n}X$$

wherein n is from 0 to 20 and X is selected from the group consisting of amino, amido, hydroxy, alkoxy, halo, mercapto, carboxy, acyl, vinyl, allyl, styryl, epoxy, isocyanato, glycidoxy, and acryloxy groups.

In one embodiment, each R group in Formulae I and II is independently an alkyl, alkoxy alkyl, aryl, aralkyl or cycloalkyl group of less than 10 carbon atoms and is more often an alkyl group containing from 1 to 5 carbon atoms or an alkoxy alkyl group containing from 2 to 10 carbon atoms.

$R^1$ in Formulae I and II is a divalent hydrocarbon or divalent polyether group containing less than 20 carbon atoms. $R^1$ can be, for example, alkylene groups such as methylene, ethylene, propylene, ethylidene and isopropylidene; cycloalkylenes such as cycloheptylene and cyclohexylene; divalent aromatic groups such as phenylene, tolylene, xylylene, and naphthalene; and divalent groups of aralkanes of the formula $$-C_6H_4-R'-$$

wherein R' is an alkylene group such as methylene, ethylene or propylene. $R^1$ also can be, for example, a divalent polyether of the formula $$R^6(OR^6)_z$$

wherein $R^6$ is an alkylene group and z is an integer of from 1 to about 5. The divalent polyether group can be, for example, diethylene ether.

$R^2$ in Formula II is a functional group which may be represented by $$C_nH_{2n}X$$

wherein n is from 0 to 20 and X is selected from the group consisting of amino, amido, hydroxy, alkoxy, halo, mercapto, carboxy, acyl, vinyl, allyl, styryl, epoxy, isocyanato, glycidoxy and acryloxy groups. The functional group $R^2$ in Formula II may be the same as the functional group (B) in Formula III described above. Accordingly, the discussion and examples of the functional group (B) in Formula III is applicable to the functional group $R^2$ in Formula II and such discussion and examples are hereby incorporated by reference.

The tris(silylorgano)amines represented by Formula I which are useful in the silane compositions of the present invention are known compounds, and procedures for preparing such tris(silylorgano)amines have been described in, for example, U.S. Pat. Nos. 5,101,055; 2,920,095; and 2,832,754; and the disclosures of these patents with regard to the tris(silylorgano)amines and methods for preparing such amines are hereby incorporated by reference.

Specific examples of tris(silylorgano)amines of Formula I which are useful in the silane compositions of the present invention include tris(trimethoxysilylmethyl)amine; tris(triethoxysilylmethyl)amine; tris(trimethoxysilylethyl)amine; tris(trimethoxysilylethyl)amine; tris(trimethoxysilylethyl)amine; tris(triethoxysilylpropyl)amine; tris(dimethoxyethoxysilylpropyl)amine; tris(tripropoxysilylpropyl)amine; etc.

As described in U.S. Pat. No. 5,101,055, the tris(silylorgano)amines may be prepared from the corresponding bis-amine by contacting the bis-amine with particulate palladium monoxide at a temperature within the range of from about 50° C. to 300° C. Another procedure for preparing the tris(silylorgano)amine compounds utilizes the reaction of the bis(trialkoxysilylalkyl)amine with an equimolar amount of a trialkylsilylpropyl halide such as the chloride. For example, tris(trimethoxysilylpropyl)amine can be prepared by reacting bis(trimethoxysilylpropyl)amine with trimethoxysilylpropyl chloride. This process is a modification of the process described in U.S. Pat. No. 4,775,415 used for preparing bis(trimethoxysilylpropyl)amine from 3-aminopropyltrimethoxysilane and 3-chloro propyltrimethoxy silane. One procedure for preparing tris(trimethoxysilylpropyl)amine is described in the S following example.

EXAMPLE A

A reaction flask is charged with 34.1 grams (0.1 mole) of bis(trimethoxysilylpropyl)amine (A-1170 from Union Carbide). The amine is heated with stirring to 132° C., and 19.8 grams (0.1 mole) of trimethoxysilylpropyl chloride are added over 15 minutes at 132–144° C. The reaction mixture is stirred for an additional hour at 140–149° C. and cooled to room temperature. Ethylenediamine (9 grams, 0.15 mole) is added at 24–26° C. and the contents are heated with stirring to 80° C. in order to assure complete reaction. The mixture is cooled to room temperature and solids are removed by filtration under vacuum. The filtrate is in two layers, and the heavier layer is separated and discarded. The remaining liquid is vacuum distilled, and the distillate is the desired product which is homogeneous and slightly yellow-brown in color.

The tris(silylorgano)compound utilized in the silane compositions of the present invention also may be an alkane characterized by the formula $$[(RO)_3Si(R^1)]_3CR^2 \tag{II}$$

wherein each R is independently alky, alkoxy alkyl, aryl, aralkyl or cycloalkyl group of less than 20 carbon atoms; $R^1$ is a divalent hydrocarbon or polyether group of less than 20 carbon atoms; and $R^2$ is a functional group represented by $$C_nH_{2n}X$$

wherein n is from 0 to 20, preferably, from 1 to 5, and X is selected from the group consisting of amino, amido, hydroxy, alkoxy, halo, mercapto, carboxy, acyl, vinyl, allyl, styryl, epoxy, isocyanato, glycidoxy and acryloxy groups. Preferred examples of R groups include methyl, ethyl, propyl, methoxymethyl, etc. The divalent hydrocarbon or divalent polyether group ($R^1$) may be any of the divalent hydrocarbon or polyether groups described above with respect to $R^1$ in Formula I. Preferred examples include methylene, ethylene, propylene, butylene, etc. Functional groups represented by $R^2$ may be any of the functional groups described above with respect to (B) in Formula III.

The amounts of the silane coupling agent A and the tris(silylorgano)amine or alkane (B) utilized in the silane compositions of the present invention may vary over a wide range. For example, the weight ratio of the silane-coupling agent (A) to the tris(silylorgano)amine or alkane (B) may range from about 1:99 and 99:1. More often, the ratio, expressed as a mole ratio of A:B, is in the range of from 1:1 to 5:1.

The silane compositions of the present invention may comprise other materials such as solvents, fillers, etc. Solvents should be capable of solubilizing both the silane coupling agent and the tris(silylorgano)amino or alkane. Typically, such solvents include lower alcohols such as methanol, butanol or isopropanol. Water, or mixtures of water and alcohols can also be used as a solvent, but the stability of such solutions is generally more limited than the solutions made with alcohols. Small portions of water can be added to the silane compositions in order to hydrolyze the conventional silane coupling agent (A) and the tris (organosilyl)amine or alkane. Alternatively, dispersions or emulsions of the silane compositions can be prepared in suitable organic solvent or mixtures of water and organic solvent. Typical solvents include, in addition to the alcohols described above, ethers, ketones, aliphatic and aromatic hydrocarbons, amides such as N,N-dimethylformamide, etc. Aqueous emulsions of the silane-coupling agents can be prepared in the conventional manner using conventional dispersants and surfactants, including nonionic surfactants.

The solids content of the silane compositions of the present invention may vary from 100% by weight in pure mixtures to as little as 0.1 weight percent or less in very dilute solutions or emulsions. More often, the solids content of solutions will be between 0.5 and 5% by weight.

A wide range of fillers can be included in the silane compositions of the present invention. The fillers may be particulate or fibrous fillers, and these include siliceous materials such as glass, quartz, ceramic, asbestos, silicone resin, glass fibers, metals such as aluminum, steel, copper, nickel, magnesium and titanium, metal oxides such as magnesium oxide, iron oxide, and aluminum oxide, and metal fibers and metal-coated glass fibers. The amount of the filler included in the silane compositions may range from 0 to about 10% by weight. When the filler is present, it is more often present in amounts of from about 0.1 to about 3% or 4% by weight.

The following examples illustrate particular embodiments of the present invention. Unless otherwise indicated in the examples and elsewhere in the specification and claims, all parts and percentages are by weight, temperatures are in degrees centigrade, and pressure is at or near atmospheric pressure.

|  | Pts./Wt. |
|---|---|
| Example 1 | |
| 3-methacryloxypropyltrimethoxy silane (A-174) | 75 |
| tris(trimethoxysilylpropyl)amine | 25 |
| Example 2 | |
| 3-methacryloxypropyltrimethoxy silane (A-174) | 75 |
| tris(trimethoxysilylpropyl)amine | 25 |
| methanol | 50 |
| Example 3 | |
| A-1160 | 19.2 |
| tris(trimethoxysilylpropyl)amine | 7.2 |
| methanol | 74.6 |

The silane compositions of the present invention can be utilized as coupling agents or adhesives in a wide variety of composite materials. In practice, the silane compositions may be applied as a liquid solution or emulsion to one surface of the two surfaces to be bonded, or the silane compositions can be applied to both of the surfaces to be bonded together. The silane compositions, particularly solutions and emulsions, can be applied to the surfaces by any conventional means such as by dipping, spraying, brushing, immersion, etc.

In one embodiment, the silane compositions of the present invention are useful for bonding a thermosetting resin surface to another resin surface which may be composed of a thermosetting resin, a thermosetting resin surface to glass, a thermosetting resin surface to metal, etc. The silane compositions of the present invention enhance the bond or peel strength between joined surfaces.

In one embodiment, the silane compositions of the present invention are useful in preparing multi-layer laminates including printed circuit boards (PCBs). Typical multi-layer laminates will comprise (A) at least one insulating layer,
(B) at least one additional layer which may be insulating or electrically conductive, and
(C) a silane layer in between the two layers.

Other multilayer laminates may comprise (A) at least one layer of an electrically conductive material;
(B) at least one layer of a dielectric material; and
(C) an adhesion-promoting layer of the silane composition of the invention positioned between and adhered to said conductive material and said dielectric material.

The adhesion-promoting layer of the silane composition of this invention enhances the bond or peel strength between the layer of conductive material (e.g., copper) and the layer of dielectric material.

(A) at least one dielectric layer having a conductive metal coating or metal circuitry on at least one surface;
(B) at least one insulating layer; and
(C) a silane layer between the surface of the dielectric layer having a conductive metal coating or metal circuitry and the insulating layer wherein said silane layer is formed from the silane compositions of the present invention and which are described more fully above.

Useful dielectric substrates or layers may be prepared by impregnating woven glass reinforcement materials with partially cured resins, usually epoxy resins (e.g., difunctional, tetrafunctional and multifunctional epoxies). Examples of useful resins include amino-type resins produced from the reaction of formaldehyde and urea, or formaldehyde and melamine, polyesters, phenolics, silicones, polyamides, polyimides, di-allyl phthalates, phenyl silanes, polybenzimidazoles, diphenyloxides, polytetrafluoroethylenes, cyanate esters, etc. These dielectric substrates often are referred to as prepregs.

The insulating layer and the dielectric layer can be prepared by impregnating woven glass reinforcement materials with partially cured resins as described above. Thus, the insulating layer or layers also may be prepregs.

In the formation of multi-layer laminates and circuit boards, several dielectric layers having a conductive metal coating or metal circuitry on at least one surface and several insulating layers may be employed.

In one example of a multi-layer laminate, the laminate can contain in order, a dielectric layer (prepreg), copper foil or copper circuitry on at least one surface of the dielectric layer, a layer of a silane composition in accordance with the present invention and an insulating layer of a thermosetting resin. Conductive metal coating or metal circuitry may be a copper sheet or foil or a copper circuitry having a thickness of at least about 4 microns coated with a layer of tin or zinc or an oxide or hydroxide of tin or zinc. The conductive metal sheets or foils and metal circuitry can be applied to the dielectric layer by techniques well known to those skilled in the art.

The metal circuitry on the dielectric layer may be obtained by conventional techniques such as by a photoimage technique of a photosensitive resist film followed by etching of the unprotected areas of metal on the dielectric layer to form electrically conductive paths or electrically conductive patterns. Etching processes are well known, and examples are described in, for example, U.S. Pat. Nos. 3,469,982 and 5,017,271 which are hereby incorporated by reference.

The metal coating or metal circuitry on the dielectric layer may be coated with a thin outer layer of a metal oxide or hydroxide such as tin oxide, hydroxide or combinations thereof. This layer which is of a thickness generally not greater than 1.5 microns and more often not greater than 1.0 micron can be formed by immersion metal plating using e.g., commercial tin-plating solutions. During and subsequent to the application of the tin, a thin coating of an oxide, hydroxide or combination thereof is formed.

A second silane adhesive-promoting layer can then be applied over the etched pattern using the techniques described above, and a second prepreg is adhered to the etched pattern. The second adhesion-promoting layer is positioned between and adhered to both the etched pattern and the second prepreg. The techniques for making multi-layer current boards also are well known in the art.

The multi-layer laminates prepared as described above may be subjected to conventional laminating temperatures and pressures between plates of laminating presses. In this manner, the laminating operation generally will involve pressures in the range of from about 250 to about 750 psi, temperatures in the range of from about 175° C. to about 350° C. and laminating cycles of from about 30 minutes to about 2 hours. The finish laminates can then be utilized in a variety of applications including printed circuit boards.

The advantages of the silane compositions of the present invention include enhanced adhesion, enhanced oxidation and enhanced moisture resistance. The improved adhesion and moisture resistance obtained with the use of the silane compositions of the present invention is demonstrated in part by the following tests and examples. The first test illustrates the improved adhesion of polymeric materials to metals. This test is a bending test designed to determine the hydrophobicity of silane compositions. Brass panels available from McGean-Rohco (Cleveland, Ohio) are cut into one-inch-wide strips, cleaned using an alkaline cleaning solution, rinsed with cold water, immersed in a commercial immersion tin solution comprising 50% v/v DuraBOND® 750A and 50% v/v DuraBOND® 750B (available from McGean-Rohco), and rinsed with cold water. The tin coated brass strips are then immersed in a 5% v/v solution of the silane composition of Example 3 adjusted to a pH of 3.5 with acetic acid. The silane-coated strips are then hot-air dried using air at 70° C., and oven-baked for one hour at 100° C. After cooling to room temperature, the silane-coated strips are placed in contact with 7658, scale flow six tetrafunctional and not fully cured glass and epoxy resin prepreg with a glassy transition temperature of 180° C. (available from Polyclad, Inc.). The strips with prepreg are pressed using a non-vacuum assisted press at 300 psi for 50 minutes at 350° C. Following the pressing, the laminates are allowed to cool to room temperature.

This procedure is then repeated using three control silane compositions identified as control Examples C-I, C-II, and C-III. The compositions of these control compositions are as follows:

| Control Examples | | |
| --- | --- | --- |
| C-I | A-1160 | 22.5 |
| | MeOH | 77.5 |
| C-II | A-1160 | 19.35 |
| | Bis(trimethoxysilyl)ethane (X1-6145A)Dow Corning | 3.87 |
| | MeOH | 76.78 |
| C-III | A-1160 | 19.24 |
| | Bis(trimethoxysilylpropyl)amine (A-1170) | 5.88 |
| | MeOH | 74.88 |

Before use, the control compositions are diluted in water at a concentration of 5% v/v and adjusted to a pH of 3.5 with acetic acid.

The bend test consists of exposing the individual strips to boiling water for various lengths of time, removing the strips from the boiling water, and then bending the strips around a Mandrel with a radius of 1 cm. The effort necessary to peel the prepreg from the surface of the metal strip is then recorded in the following manner.

| Rating | Explanation |
| --- | --- |
| 4 | Cannot peel prepreg from metal |
| 3 | Bulk of the prepreg peels away and leaves a layer of prepreg uniformly on the surface of the metal |

-continued

| Rating | Explanation |
| --- | --- |
| 2 | Bulk of the prepreg peels away and leaves more than 50% of the areas prepreg on surface of the metal |
| 1 | Bulk of the prepreg peels away and leaves less than 50% of the areas prepreg on surface of the metal |
| 0 | Prepreg peels away from the metal and the resulting metal surface has no prepreg attached |

In one series, the silane solutions used to coat the brass strips were solutions used immediately on formation. In the second series, the silane solutions were aged six weeks before being used to coat the brass strips. The results of the bend and peel test are summarized in the following Table II.

TABLE II

| | Bend and Peel Test | | |
| --- | --- | --- | --- |
| | | Results | |
| Example | 2 hrs. | 24 hrs. | 48 hrs. |
| Fresh Solutions: | | | |
| 3 | 4 | 3 | 3 |
| C-I | 0 | 0 | 0 |
| C-II | 4 | 3 | 3 |
| C-III | 4 | 3 | 1 |
| Aged Solutions: | | | |
| 3 | 3 | 3 | 3 |
| C-I | 0 | 0 | 0 |
| C-II | 4 | 2 | 1 |
| C-III | 3 | 3 | 1 |

The improved adhesion obtained with the silane compositions of the present invention also is demonstrated by conducting a pull strength test performed in accordance with IPC-TM-650 and MIL-P-13949G. Two test methods are utilized: a dip test and a spray test. In the dip test, a copper foil (1 ounce, single treat) is cleaned, etched, coated with an immersion tin solution (as described above in the bend test), and solutions of silanes and mixtures of silanes are applied by dipping the foil into the solutions of the silane. The foil is then air dried and baked for one hour at 100° C. The coated foil is laminated to 1080 scale flow 3 prepreg (Polyclad) using a non-vacuum assisted press heated to 350° C. adjusted to press at 300 psi for 50 minutes. Following the pressing cycle, the laminated foils are air-cooled for 75 minutes.

In the spray test, the above procedure for the dip test is repeated except that the solutions containing the silane coupling agents and cross-linking agents are spray applied, wiped by rollers and then air-dried.

As mentioned above, the pull test is performed in accordance with IPC-TM-650 and MIL-P-13949G. The results are the combined average strength of the adhesive bonds, in psi, as a function of the distance the foils are pulled along an axis of similarly treated laminates. The results of the pull strength test are summarized in the following Table III. All results are the average values of three tests, on three panels, each test comprising 500 measurements along the length of the pulled foil.

TABLE III

Pull Strength Test

| Example | Method | Average Pull Strength | Standard Deviation |
|---|---|---|---|
| 3 | dip | 5.4 | 0.14 |
| C-I | dip | 4.98 | 0.29 |
| C-II | dip | 5.46 | 0.27 |
| C-III | dip | 4.4 | 0.28 |
| 3 | spray | 6.9 | 0.2 |
| C-II | spray | 7.0 | 0.2 |
| 3 | spray after six weeks | 7.7 | 0.15 |
| C-II | spray after six weeks | 6.3 | 0.14 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A silane composition comprising
(A) a silane coupling agent; and
(B) a tris(silylorgano)amine or alkane characterized by the formulae $$[(RO)_3SiR^1]_3N \qquad (I)$$

or $$[(RO)_3SiR^1]_3CR^2 \qquad (II)$$

wherein each R is independently an alkyl, alkoxyalkyl, aryl, aralkyl or cycloalkyl group of less than 20 carbon atoms; $R^1$ is a divalent hydrocarbon or polyether group of less than 20 carbon atoms; and $R^2$ is a functional group represented by $$C_nH_{2n}X$$

wherein n is from 0 to 20 and X is selected from the group consisting of amino, amido, hydroxy, alkoxy, halo, mercapto, carboxy, acyl, vinyl, allyl, styryl, epoxy, isocyanato, glycidoxy, and acryloxy groups.

2. The silane composition of claim 1 wherein (B) is a tris(silylorgano)amine characterized by Formula I.

3. The silane composition of claim 1 wherein each R is independently an alkyl group.

4. The silane composition of claim 1 wherein each R is independently an alkyl group containing from 1 to 5 carbon atoms.

5. The silane composition of claim 1 wherein $R^1$ is a divalent hydrocarbon group containing up to about 8 carbon atoms.

6. The silane composition of claim 1 wherein the silane coupling agent (A) is characterized by the formula $$A_{(4-x)}Si(B)_x \qquad (III)$$

wherein A is a hydrolyzable group, x is 1, 2 or 3, and B is an alkyl or aryl group or a functional group represented by the formula $$C_nH_{2n}X$$

wherein n is from 0 to 20 and X is selected from the group consisting of amino, amido, hydroxy, alkoxy, halo, mercapto, carboxy, acyl, vinyl, allyl, styryl, epoxy, isocyanato, glycidoxy, and acryloxy groups.

7. The silane composition of claim 6 wherein each A is an RO group wherein each R is independently an alkyl, aryl, aralkyl or cycloalkyl group containing less than 20 carbon atoms, and x=1.

8. The silane composition of claim 7 wherein each R in Formula III is an alkyl group containing up to about 5 carbon atoms.

9. The silane composition of claim 6 wherein B in Formula III is represented by the formula $$C_nH_{2n}X$$

wherein n is an integer from 1 to 5 and X is an amido group.

10. The silane composition of claim 6 wherein B in Formula III is an amino group.

11. The silane composition of claim 1 wherein the mole ratio of A:B is in the range of from 1:1 to 5:1.

12. A silane composition comprising
(A) a silane coupling agent; and
(B) a tris(silylorgano)amine characterized by the formula $$[(RO)_3SiR^1]_3N \qquad (I)$$

wherein each R is independently an alkyl group containing from 1 to about 5 carbon atoms; and $R^1$ is a divalent hydrocarbon group containing from 1 to about 5 carbon atoms.

13. The silane composition of claim 12 wherein each R is a methyl or ethyl group.

14. The silane composition of claim 12 wherein each $R^1$ contains from 1 to about 4 carbon atoms.

15. The silane composition of claim 12 wherein the silane coupling agent (A) is characterized by the formula $$(RO)_3SiB \qquad (IIIA)$$

wherein each R is independently an alkyl, aryl, aralkyl or cycloalkyl group of less than 20 carbon atoms; and B is a functional group represented by $$C_nH_{2n}X$$

wherein n is from 0 to 20 and X is selected from the group consisting of amino, amido, hydroxy, alkoxy, halo, mercapto, carboxy, acyl, vinyl, allyl, styryl, epoxy, isocyanato, glycidoxy, and acryloxy groups.

16. The silane composition of claim 15 wherein n is an integer from 1 to about 5, and X is an amino or amido group.

17. The silane composition of claim 12 wherein the silane coupling agent (A) is characterized by the formula $$(RO)_3Si-R^4N(H)CONH_2 \qquad (IIIB)$$

wherein each R is independently an alkyl group containing 1 to about 5 carbon atoms, and $R^4$ is a divalent hydrocarbyl group containing from 1 to about 5 carbon atoms.

18. The silane composition of claim 17 wherein each R is a methyl or ethyl group.

19. A silane composition comprising
(A) a silane coupling agent characterized by the formula $$(RO)_3SiR^4N(H)CONH_2 \qquad (IIIB)$$

wherein each R is a methyl or ethyl group, and $R^4$ is a divalent hydrocarbyl group containing from 1 to about 5 carbon atoms; and (B) a tris(silylorgano)amine characterized by the formula $$[(RO)_3SiR^1]_3N \qquad (I)$$

wherein each R is a methyl or ethyl group and each $R^1$ is independently a divalent hydrocarbyl group containing from 1 to about 4 carbon atoms.

20. The silane composition of claim 19 wherein each R in Formulae IIIB and I is a methyl group.

21. The silane composition of claim 19 wherein the mole ratio of A to B is from about 1:1 to about 5:1.

22. A silane composition comprising
   (A) a silane coupling agent; and
   (B) a tris(silylorgano)alkane characterized by the formula $$[(RO)_3SiR^1]_3CR^2 \qquad (II)$$

wherein each R is independently an alkyl, alkoxyalkyl, aryl, aralkyl or cycloalkyl group of less than 20 carbon atoms; $R^1$ is a divalent hydrocarbon or polyether group of less than 20 carbon atoms; and $R^2$ is a functional group represented by $$C_nH_{2n}X$$

wherein n is from 0 to 20 and X is selected from the group consisting of amino, amido, hydroxy, alkoxy, halo, mercapto, carboxy, acyl, vinyl, allyl, styryl, epoxy, isocyanato, glycidoxy, and acryloxy groups.

23. The silane composition of claim 22 wherein each R is independently an alkyl group.

24. The silane composition of claim 22 wherein each R is independently an alkyl group containing from 1 to 5 carbon atoms.

25. The silane composition of claim 22 wherein each $R^1$ is a divalent hydrocarbon group containing up to about 8 carbon atoms.

26. The silane composition of claim 22 wherein the silane coupling agent (A) is characterized by the formula $$(RO)_3SiB \qquad (IIIA)$$

wherein each R is independently an alkyl, aryl, aralkyl or cycloalkyl group of less than 20 carbon atoms; and B is a functional group represented by $$C_nH_{2n}X$$

wherein n is from 0 to 20 X is selected from the group consisting of amino, amido, hydroxy, alkoxy, halo, mercapto, carboxy, acyl, vinyl, allyl, styryl, epoxy, isocyanato, glycidoxy, and acryloxy groups.

* * * * *